United States Patent [19]
Seino et al.

[11] Patent Number: 5,917,027
[45] Date of Patent: Jun. 29, 1999

[54] NUCLEIC ACIDS ENCODING POTASSIUM-CHANNEL PROTEINS

[75] Inventors: Susumu Seino; Nobuya Inagaki, both of Chiba, Japan

[73] Assignees: Susumu Seino, Chiba; JCR Pharmaceuticals Co., Ltd., Hyogo, both of Japan

[21] Appl. No.: 08/614,156

[22] Filed: Mar. 12, 1996

[30] Foreign Application Priority Data

Sep. 18, 1995 [JP] Japan .................................. 7-264943

[51] Int. Cl.⁶ ............................ C12N 15/12; C12N 15/63; C12N 1/21; C12N 5/10
[52] U.S. Cl. ....................... 536/23.4; 536/23.1; 536/23.5; 435/320.1; 435/252.3; 435/254.11; 435/325; 435/410
[58] Field of Search .................................. 536/23.1, 23.4, 536/24.3, 24.31, 24.32, 23.5; 435/320.1, 69.1, 172.3, 252.3, 254.11, 325, 410, 6; 800/2, 200

[56] References Cited

FOREIGN PATENT DOCUMENTS

94/19464 9/1994 WIPO .
95/04820 2/1995 WIPO .

OTHER PUBLICATIONS

"The Journal of Biochemical Chemistry", vol. 270, No. 11, issue of Mar. 17, 1995.

Research Articles, Science vol. 270 Nov. 17, 1995.

FEBS LETT, Jun. 26, 1995, 367, P193–7, Netherlands, XP002019858 Sakura H et al: "Characterization and variation of a human inwardly–rectifying–K–channel gene (KCNJ6): a putative ATP–sensitive K–channel subunit.".

Diabetes, May 1995, 44 (5) P592–6, United States, XP000611937, Tsaur ML et al: "Isolation of a cDNA clone encoding a KATP channel–like protein expressed in insulin–secreting cells, localization of the human gene to chromosome band 21q22.1, and linkage studies with NIDDM."

Biochem Biophys Res Commun, Jul. 26, 1995, 212 (3) P894–9, United States, XP002019859, Stoffel M et al: "Cloning of rat KATP–2 channel and decreased expression in pancreatic islets of male Zucker diabetic fatty rats."

J. Biol Chem, Mar. 17, 1995, 270 (11) P5691–4, United States, XP002019860, Susumu Seino Inohana Shukusha Chiba University: "Cloning and functional characterization of a novel ATP–sensitive potassium channel ubiquitously expressed in rat tissues, including pancreatic islets, pituitary, skeletal muscle, and heart."

Science, Apr. 21, 1995, 268 (5209) P423–6, United States, XP 002019861; Aguilar–Bryan L et al: "Cloning of the beta cell high–affinity sulfonylurea receptor: a regulator of insulin secretion [see comments]."

Science, Nov. 17, 1995, 270 (5239) P1166–70, United States, XP002019862, Inagaki N et al: "Reconstitution of IKATP: an inward rectifier subunit plus the sulfonylurea receptor [see comments]."

Asford et al. Nature 370:456–459, Aug. 1994.

Bowie et al. Science 247:1306–1310, 1990.

Wells. Biochemistry 29:8509–8517, 1990.

Ngo et al. The Protein Folding Problem and Tertiary Structure Prediction, Merz et al., eds., Birkhauser, Boston, pp. 492–495, 1994.

*Primary Examiner*—Elizabeth C. Kemmerer
*Attorney, Agent, or Firm*—Jacobson, Price, Holman & Stern, PLLC

[57] ABSTRACT

The present invention provides DNAs of hβIR and mβIR, which are novel ATP-sensitive potassium channels being present specifically in the pancreatic cells, and proteins encoded by such DNAs, wherein by utilizing them, it is possible to produce said proteins in large quantities through the known genetic engineering techniques for use as a reagent in the research work as well as in the diagnosis and therapy for diabetes and other diseases.

11 Claims, 8 Drawing Sheets

FIG. 1

|  10        |  20        |  30        |  40        |  50        |  60        |
| MLSRKGIIPE | EYVLTRLAED | PAEPRYRARQ | RRARFVSKKG | NCNVAHKNIR | EQGRFLQDVF |
|  70        |  80        |  90        | 100        | 110        | 120        |
| TTLVDLKWPH | TLLIFTMSFL | CSWLLFAMAW | WLIAFAHGDL | APSEGTAEPC | VTSIHSFSSA |
| 130        | 140        | 150        | 160        | 170        | 180        |
| FLFSIEVQVT | IGFGGRMVTE | ECPLAILSLI | VQNIVGLMIN | AIMLGCIFMK | TAQAHRRAET |
| 190        | 200        | 210        | 220        | 230        | 240        |
| LIFSKHAVIA | LRHGRLCFML | RVGDLRKSMI | ISATIHMQVV | RKTTSPEGEV | VPLHQVDIPM |
| 250        | 260        | 270        | 280        | 290        | 300        |
| ENGVGGNSIF | LVAPLIIYHV | IDANSPLYDL | APSDLHHHQD | LEIIVILEGV | VETTGITTQA |
| 310        | 320        | 330        | 340        | 350        | 360        |
| RTSYLADEIL | WGQRFVPIVA | EEDGRYSVDY | SKFGNTIKVP | TPLCTARQLD | EDHSLLEALT |
| 370        | 380        | 390        | 400        | 410        | 420        |
| LASARGPLRK | RSVPMAKAKP | KFSISPDSLS | *........  | .........  | .........  |

FIG. 3

|  10        |  20        |  30        |  40        |  50        |  60        |
| MLSRKGIIPE | EYVLTRLAED | PAEPRYRTRE | RRARFVSKKG | NCNVAHKNIR | EQGRFLQDVF |
|  70        |  80        |  90        | 100        | 110        | 120        |
| TTLVDLKWPH | TLLIFTMSFL | CSWLLFAMVW | WLIAFAHGDL | APGEGTNVPC | VTSIHSFSSA |
| 130        | 140        | 150        | 160        | 170        | 180        |
| FLFSIEVQVT | IGFGGRMVTE | ECPLAILILI | VQNIVGLMIN | AIMLGCIFMK | TAQAHRRAET |
| 190        | 200        | 210        | 220        | 230        | 240        |
| LIFSKHAVIT | LRHGRLCFML | RVGDLRKSMI | ISATIHMQVV | RKTTSPEGEV | VPLHQVDIPM |
| 250        | 260        | 270        | 280        | 290        | 300        |
| ENGVGGNGIF | LVAPLIIYHV | IDSNSPLYDL | APSDLHHHQD | LEIIVILEGV | VETTGITTQA |
| 310        | 320        | 330        | 340        | 350        | 360        |
| RTSYLADEIL | WGQRFVPIVA | EEDGRYSVDY | SKFGNTIKVP | TPLCTARQLD | EDRSLLDALT |
| 370        | 380        | 390        | 400        | 410        | 420        |
| LASSRGPLRK | RSVAVAKAKP | KFSISPDSLS | *........  | .........  | .........  |

FIG. 2

```
         10         20         30         40         50         60
 ATGCTGTCCC GCAAGGGCAT CATCCCCGAG GAATACGTGC TGACACGCCT GGCAGAGGAC 70         80         90        100        110        120
 CCTGCCGAGC CCAGGTACCG TGCCCGCCAG CGGAGGGCCC GCTTTGTGTC CAAGAAAGGC 130        140        150        160        170        180
 AACTGCAACG TGGCCCACAA GAACATCCGG GAGCAGGGCC GCTTCCTGCA GGACGTGTTC 190        200        210        220        230        240
 ACCACGCTGG TGGACCTCAA GTGGCCACAC ACATTGCTCA TCTTCACCAT GTCCTTCCTG 250        260        270        280        290        300
 TGCAGCTGGC TGCTCTTCGC CATGGCCTGG TGGCTCATCG CCTTCGCCCA CGGTGACCTG 310        320        330        340        350        360
 GCCCCCAGCG AGGGCACTGC TGAGCCCTGT GTCACCAGCA TCCACTCCTT CTCGTCTGCC 370        380        390        400        410        420
 TTCCTTTTCT CCATTGAGGT CCAAGTGACT ATTGGCTTTG GGGGCGCAT GGTGACTGAG 430        440        450        460        470        480
 GAGTGCCCAC TGGCCATCCT GAGCCTCATC GTGCAGAACA TCGTGGGGCT CATGATCAAC 490        500        510        520        530        540
 GCCATCATGC TTGGCTGCAT CTTCATGAAG ACTGCCCAAG CCCACCGCAG GGCTGAGACC 550        560        570        580        590        600
 CTCATCTTCA GCAAGCATGC GGTGATCGCT CTGCGCCACG GCCGCCTCTG CTTCATGCTA 610        620        630        640        650        660
 CGTGTGGGTG ACCTCCGCAA GAGCATGATC ATCAGCGCCA CCATCCACAT GCAGGTGGTA 670        680        690        700        710        720
 CGCAAGACCA CCAGCCCCGA GGGCGAGGTG GTGCCCCTCC ACCAGGTGGA CATCCCCATG 730        740        750        760        770        780
 GAGAACGGCG TGGGTGGCAA CAGCATCTTC CTGGTGGCCC CGCTGATCAT CTACCATGTC 790        800        810        820        830        840
 ATTGATGCCA ACAGCCCACT CTACGACCTG GCACCCAGCG ACCTGCACCA CCACCAGGAC 850        860        870        880        890        900
 CTCGAGATCA TCGTCATCCT GGAAGGCGTG GTGGAAACCA CGGGCATCAC CACCCAGGCC 910        920        930        940        950        960
 CGCACCTCCT ACCTGGCCGA TGAGATCCTG TGGGGCCAGC GCTTTGTGCC CATTGTAGCT 970        980        990       1000       1010       1020
 GAGGAGGACG GACGTTACTC TGTGGACTAC TCCAAGTTTG GCAACACCAT CAAAGTGCCC 1030       1040       1050       1060       1070       1080
 ACACCACTCT GCACGGCCCG CCAGCTTGAT GAGGACCACA GCCTACTGGA AGCTCTGACC 1090       1100       1110       1120       1130       1140
 CTCGCCTCAG CCCGCGGGCC CCTGCGCAAG CGCAGCGTGC CCATGGCCAA GGCCAAGCCC 1150       1160       1170       1180       1190       1200
 AAGTTCAGCA TCTCTCCAGA TTCCCTGTCC TGA...............    ....................     ....................
```

FIG. 4

```
         10         20         30         40         50         60
ATGCTGTCCC GAAAGGGCAT TATCCCTGAG GAATATGTGC TGACCCGGCT GGCAGAGGAC
         70         80         90        100        110        120
CCTGCAGAGC CCAGGTACCG TACTCGAGAG AGGAGGGCCC GCTTCGTGTC CAAGAAAGGC
        130        140        150        160        170        180
AACTGCAACG TCGCCCACAA GAACATTCGA GAGCAGGGCC GCTTCCTGCA GGATGTGTTC
        190        200        210        220        230        240
ACCACGCTGG TGGACCTCAA ATGGCCACAC ACTCTGCTCA TTTTCACCAT GTCCTTCCTG
        250        260        270        280        290        300
TGCAGCTGGC TGCTCTTTGC CATGGTCTGG TGGCTCATCG CCTTCGCCCA CGGTGACCTG
        310        320        330        340        350        360
GCCCCCGGAG AGGGCACCAA TGTGCCCTGC GTCACAAGCA TCCACTCCTT TTCATCTGCC
        370        380        390        400        410        420
TTCCTTTTCT CCATCGAGGT CCAGGTGACC ATTGGTTTCG GCGGGCGCAT GGTGACAGAG
        430        440        450        460        470        480
GAATGTCCCC TGGCCATCCT CATTCTCATT GTGCAGAATA TCGTCGGGCT GATGATCAAC
        490        500        510        520        530        540
GCCATCATGC TGGGCTGCAT CTTCATGAAA ACGGCCCAGG CCCATCGGCG GGCAGAAACC
        550        560        570        580        590        600
CTCATCTTCA GCAAGCATGC TGTGATCACC CTGCGCCATG GCCGCCTGTG CTTCATGCTG
        610        620        630        640        650        660
CGCGTAGGGG ACCTCCGAAA GAGCATGATC ATTAGCGCCA CCATCCACAT GCAGGTGGTG
        670        680        690        700        710        720
CGCAAGACCA CCAGCCCCGA GGGCGAAGTT GTGCCTCTCC ACCAGGTAGA CATCCCCATG
        730        740        750        760        770        780
GAGAATGGCG TGGGTGGTAA CGGCATCTTC CTGGTGGCCC CACTCATCAT CTACCACGTC
        790        800        810        820        830        840
ATCGACTCCA ACAGCCCGCT CTACGACCTG GCTCCTAGTG ACCTGCACCA CCACCAGGAC
        850        860        870        880        890        900
CTGGAGATCA TTGTCATCTT GGAAGGCGTG GTAGAAACCA CGGGCATCAC CACCCAGGCC
        910        920        930        940        950        960
CGCACCTCCT ACCTAGCTGA CGAGATTCTA TGGGGCAGC GCTTTGTCCC CATTGTGGCC
        970        980        990       1000       1010       1020
GAGGAGGACG GCCGCTATTC TGTGGACTAC TCCAAATTTG GTAACACCAT TAAAGTGCCC
       1030       1040       1050       1060       1070       1080
ACACCACTCT GCACAGCCCG CCAGCTTGAT GAGGACCGCA GTCTGCTGGA TGCCCTGACC
       1090       1100       1110       1120       1130       1140
CTCGCCTCGT CGCGGGGGCC CCTGCGCAAG CGCAGTGTGG CTGTGGCGAA GGCCAAGCCC
       1150       1160       1170       1180       1190       1200
AAGTTTAGCA TCTCTCCAGA TTCCTTGTCC TGA.............  .................  ..................
```

FIG. 6

| Subregion | Sense primer | | Antisense primer | | Fragment size |
|---|---|---|---|---|---|
| A | CCGAGAGGACTCTGCAGTGA | -86 to -66 | CACCAGCGTGGTGAACACGT | 193 to 173 | 279 |
| B | GAAAGGCAACTGCAACGTGG | 114 to 134 | TAGTCACTTGGACCTCAATG | 392 to 372 | 279 |
| C | CTGTGTCACCAGCATCCACT | 327 to 347 | TGATGATCATGCTCTTGCGG | 635 to 615 | 309 |
| D | TCAGCAAGCATGCGGGTGATC | 548 to 568 | ACGCCTTCCAGGATGACGAT | 870 to 850 | 323 |
| E | CTACCATGTCATTGATGCCA | 771 to 791 | GCACTTTGATGGTGTTGCCA | 1019 to 999 | 249 |
| F | CGTTACTCTGTGGACTACTC | 973 to 993 | TGGGCTACATACCACATGGT | 1236 to 1216 | 264 |

FIG. 8A
FIG. 8B

NUCLEIC ACIDS ENCODING POTASSIUM-CHANNEL PROTEINS

The present invention relates to proteins for novel ATP-sensitive potassium channels (βIR) that are expressed in the pancreatic β-cells and insulin-secreting cell lines of human and mouse origins, and to genes encoding the same, wherein the said proteins and genes are useful as diagnostic and therapeutic agents for diabetes and the like and also in the development of such agents.

BACKGROUND OF THE INVENTION

The etiology for diabetes is known to be mostly owing to disturbances of insulin secretion in the pancreatic β-cells. Consequently, elucidation of the molecular mechanism of insulin secretion is expected to play an important role in the clarification of causes for diabetes and the development of therapeutic agents against diabetes, but no detail has yet been made known on such molecular mechanism.

It has been made clear that the ATP-sensitive potassium channel ($K_{ATP}$ channel) being present on the cellular membrane plays a leading role in the cellular functions such as secretions and muscular contraction by conjugating the state of metabolism in the cells with the membrane potential. For example, the $K_{ATP}$ channel has been confirmed to be present in the cardiac muscle in 1983 [Noma, A., Nature 305:147 (1983)] the pancreatic β-cell [Cook; D. L. et al., Nature 311:271 (1984), Misler, S. et al., Proc. Natl. Acad. Sci. U.S.A. 83:7119 (1986)], pituitary [Bernardi, H. et al., Proc. Natl. Acad. Sci U.S.A., 90:1340 (1993)]. skeletal muscle [Spruce, A. E., et al., Nature, 316: 736 (1985)], etc.

In the pancreatic β-cells, particularly, ATP produced by the metabolism of glucose brings about ion inflow from the calcium channel by closing the $K_{ATP}$ channel to cause depolarization, resulting in secretion of insulin. As is evident from this, the $K_{ATP}$ channel plays a leading role in regulating the secretion of insulin.

The $K_{ATP}$ channel belongs to a potassium channel family exhibiting electrophysiologically inward rectification, whereby the potassium channel family exhibiting inward rectification is classified into the five subfamilies (ROMK1, IRK1, GIRK1 and $cK_{ATP}$-1 and $uK_{ATP}$-1) on the basis of the degree of amino acid sequence identity.

Nevertheless, there has not been clarified the molecular architecture for the $K_{ATP}$ channel in the pancreatic β-cells. $uK_{ATP}$-1 that has been found by the present inventors to be ubiquitous in various tissues is expressed in the normal tissues including the pancreatic β-cells but not expressed in the insulin-secreting cell line.

In view of the above, the present inventors searched into a potassium channel which is to be expressed specifically in the pancreatic β-cells and insulin-secreting cell line.

The novel ATP-sensitive potassium channel that is expressed specifically in the pancreatic β-cells has not yet been clarified for its detailed protein structure, while no information has been disclosed on the formation of complexes with other proteins, for example, the novel potassium channel ($uK_{ATP}$-1) being ubiquitous in tissues and sulfonylurea binding protein.

SUMMARY OF THE INVENTION

In order to achieve the isolations identification and functional analyses of a novel $K_{ATP}$ channel, there are required the highly sophisticated techniques, such as molecular biological technique, cellular biological technique and electrophysiological technique.

Such being the case, the present inventors made ample and full use of such techniques to isolate human and rat genomes encoding an isoform of the novel $K_{ATP}$ channel (βIR) expressed in the pancreatic β-cells and insulin-secreting cell lines of man and rats and cDNAs and also to identify their amino acid sequences (refer to FIGS. 1, 2, 3 and 4). After the identified βIR channel protein was expressed in the Xenopus oocyte and mammalian cell lines, electrophysiological analysis demonstrated that the βIR channel is an ATP-sensitive potassium channel exhibiting inward rectification.

The proteins of the present invention are novel ATP-sensitive potassium channels (βIR) that are expressed specifically in the pancreatic β-cells and insulin-secreting cells of mammalians and are an isoform of the novel ATP-sensitive potassium channel $uK_{ATP}$-1 being ubiquitously present and expressed in various tissues.

The present invention embraces the amino acid sequences for such proteins, the coding DNA base sequences, plasmid having such sequences incorporated therein and furthermore recombinant cells (transformants) having such plasmid incorporated therein. In addition, this invention embraces the isolated βIR genes and proteins and their recombinant proteins, their related materials such as agonists and antagonists, and drug designs inclusive of diagnostics and drugs for gene therapy.

DETAILED DESCRIPTION

The hβIR of a human origin and the mβIR of a mouse origin being specific to the pancreatic β-cells are composed of 390 amino acid residues [including Met (initiation codon ATG)], with their molecular weights being 43,512 daltons and 43,559 daltons, respectively. wherein they show 96% amino acid sequence identity. Furthermore, the βIRs of human and rat origins exhibit 98% amino acid sequence identity with $uK_{ATP}$-1 of a mouse origins as well as 46%, 41%, 42% and 44 5 amino acid sequence identity individually with other potassium channels, IRK1, ROMK1, GIRK1 and $cK_{ATP}$-1 indicating that βIRs, belonging to the same subfamily as $uK_{ATP}$-1, are the isoform.

Also, it was confirmed that, in place of the Gly-Tyr-Gly motif (amino acid 132–134) retained in the pore portion (H5 segment) of the presently identified inward rectifier potassium channels, the βIR of the present invention as well as $uK_{ATP}$-1 retain a Gly-Phe-Gly motif in common.

With reference to the aspartate (Asn) which is a crucial determinant for the inward rectifier potassium channels, $uK_{ATP}$-1 has Asn-163 and βIR has Asn-153 in the second transmembrane segment, respectively. βIR shows high homology with $uK_{ATP}$-1 but there is no intracellular similarity between the amino-terminated and carboxyl-terminated regions and the pore forming segment (H5). In the intracellular regions of βIRs of human and mouse origins, there are two potential cAMP dependent protein kinase phosphorylation sites (Thr-224 and Ser-372) and five protein-kinase-C dependent phosphorylation sites (Ser-3, Ser-37, Thr-336, Thr-345 and Ser-363), as well as three potential casein-kinase II dependent phosphorylation sites (Thr-62, Thr-224 and Ser-354), with no N-linked glycosylation site in the extracellular region.

RNA blotting studies revealed that mRNA of βIR is expressed at high levels of frequency in the pancreatic β-cells and insulin-secreting cell line but at low levels in such tissues as the heart, skeletal muscle and brain. In order to characterize the functional properties of βIR channel, furthermore, hβIR and mβIR were expressed in *Xenopus laevis* oocytes.

In man and mice, the in vitro synthesized cRNA was expressed, resulting in significantly increased inflow of inward rectifier potassium channel as compared with a control treated through injection of water.

AS is described above, βIR shows a high homology with uK$_{ATP}$-1 and its MRNA is expressed markedly in the pancreatic β-cells and insulin-secreting cell line, thus raising the possibility that βIR would be a major ATP-sensitive potassium channels in the pancreatic β-cells. In the research studies of the present invention, βIR was found to be inhibited by sulfonylurea drugs being currently put in extensive use as a therapeutic agent against diabetes which finding contributed to recognize the importance of AIR in the pancreatic β-cells.

Particularly, co-expression of βIR and sulfonylurea receptor demonstrated that the channel (βIR) exhibits ATP sensitivity together with its activity being inhibited by sulfonylurea drugs.

Consequently, it is suggested that βIR and sulfonylurea receptor cooperate to form a complex in vivo to develop the function.

DNAs of novel hβIR and mβIR according to the present invention were obtained from a cDNA library and genom library. The genome genes of hβIR and rβIR are characterized by the absence of intron and are localized at the chromosome lip 15.1.

The genome DNA of hβIR and rβIR can also be obtained by probing the genome libraries with use of their cDNAs and their fragments.

The isolated DNA of hβIR can easily be subjected to deletion, insertion and replacement by the known techniques to prepare its mutants.

For example, the motif being characteristic to the pore segment of βIR can be deleted or replaced with other amino acid to prepare a homologue of βIR. A homologue having the motif deleted is capable of bonding to a sulfonylurea drug but does not possess the channel function. There is a possibility for a homologue of βIR to be given as a neutralizing agent a patient with diabetes having an excessive intake of a sulfonylurea drug. Moreover, it is possible to prepare a potassium channel protein showing more potent inward rectification by the replacement of a motif segment of βIR.

Elucidation of the amino acid sequence of βIR facilitate more effective but less toxic βIR inhibitor to be developed. The present invention embraces the preparation of mutants of βIR and their agonists and antagonists.

By utilizing the known techniques, furthermore it is easy to link nucleotide sequences encoding other proteins and synthetic polypeptides to DNA of hβIR or its DNA mutants at the amino terminal or carboxyl terminal to thereby prepare fusion proteins, namely derivatives of βIR. For example, such fusion proteins are prepared in the form of a precursor protein and undergo cleavage in vivo or in vitro to develop their functions. it is possible to confer to the fusion proteins the tissue targeting or membrane orientating property, in addition to their originally inherent function. In such a case, it is understood to be comprehended in the scope of the invention to contain sugar-linking amino acids into such fusion proteins to thereby form a novel sugar bond, providing the tissue/membrane orientating property. Also, the present invention comprises the preparation of fusion proteins containing βIR.

Preparation of mutants or derivatives of βIR constitutes a technique being well known for the utilization of the partially specific mutation technique [Adelman et al, DNA, 2:183 (1983)].

In order to produce hβIR and mβIR, their mutants and their derivatives in large quantities, there are prepared reproducible recombinant plasmids encoding such DNAs based on the known technique, and then, such plasmids are used to prepare transformed cells, followed by cultivation of these host cells, wherein such host cells involve microorganisms, yeasts and animal cells.

Prokaryotes such as bacteria are suited for cloning of deoxyribonucleotides. For example, pBR322 plasmid derived from E. coli contains a gene resistant to ampicillin and tetracycline and can provide a practical means of identifying transformed cells. Additionally, microbial plasmids contain a promoter which is usable to express their own proteins. In addition to prokaryotes, eukaryotes such as yeasts can work well.

Especially, a plasmid YRp7 is utilizable commonly in the expression in yeasts of the species Saccharomyces [Stinchomb et al., Nature, 282:39 (1979)].

Animal cells are also used as a host, and particularly the incubation of vertebra cells is employable easily and constitutes a conventional means [Krause and Paterson, Tissue Culture, Academic Press (1973)]. As the cell lines, there are mentioned AtT-20, Hela cells, Chinese hamster ovary (CHO), COMSM6, COS-7 and the like. The promoters of Polyomavirus, Adenovirus 2, Cytomegalovirus and Simian virus 40 are used to control the function of expression plasmid in such cell lines, wherein pCMV is a plasmid which finds widened application in the expression systems of animal cells [Thomsen et al., PNAS, 81: 659 (1984)].

The DNA sequences for the channel protein and hβIR and mβIR according to the present invention begin with the initiation codon "ATG". In cases where the recombinant cells are used to synthesize such channel proteins there is no need to add ATG to the desired DNA, thus making the manipulation easy. When βIR is expressed in a prokaryote transformed with E. coli, consequently, there is generally synthesized a protein of the amino acid sequence beginning with Met. The N-terminated Met of the resultant protein may be eliminated depending upon the purpose of application.

In cases in which βIR is synthesized in recombinant animal cells, similarly, a protein βIR (1–390) having Met contained at the N-terminal or a protein βIR (2–390) having Met eliminated at the N-terminal is bio-synthesized, and both are useful for individually intended application purposes.

hβIR and its fragments can be administered to animals for their immunization to thereby produce antibodies. Also, immunization of animals permits a monoclonal antibody to be produced from cells secreting the desired antibody.

It has become easy to prepare hβIR in large quantities, thus providing better understanding of the same at the molecular level. Accordingly, the exploitation of hβIR and its mutants or analogs raises the possibility to develop reagents for research, diagnostics or therapeutics mainly for the diabetic disease.

Among others βIR proteins are suited for diagnostics and therapeutics. Namely, such proteins can be utilized in the procedures of investigating into a substance that exerts agonistic or antagonistic action on βIR. By expressing βIR in animal cells, for example, a substance acting to promote or inhibit their activities can be analyzed and tested [Kayano, T. et al., J. Biol. Chem., 265: 13276 (1990), Example 4].

Additionally the pertinent information has been obtained on the DNA sequences of βIR, facilitating deoxyribonucleotides for fractional sequences to be prepared. Such relatively short DNA sequences possess the capability to hybridize with the gene to be selected, and can find application as a probe for nucleic acids. For the purpose of examining the hybridization the appropriate labeling means utilizing radioactive substances or enzymes as a label are available as a known technique, and probes are effective for detection of complementary DNAs in different tissues.

Accordingly, the probes as prepared with use of βIR can be used to produce nucleic acids capable of hybridization from various organisms and their tissues. The resultant nucleic acids may be the same as βIR or its isoform or analogs, while the prepared probes are utilizable in the gene diagnosis for patients; investigation can be conducted into patients nucleotide sequences hybridized with such probe to detect the disease gene.

The blocker agent (sulfonylurea) for the potassium channel has heretofore been used as a therapeutic against diabetes, and hβIR and its mutants, derivatives and monoclonal antibodies to them, as well as agonists and antagonists related to them, can be processed into pharmaceutical preparations to give therapeutic drugs against diabetes, While in the case of functional deficiency of hβIR itself, they can be used in the substitution therapy to thereby make up for such deficient function.

The gene for hβIR, after being transfected into a vector or stem cells, can be administered to human beings in expectation of a drug for gene therapy.

Below described are the examples to illustrate the invention in more detail, while refering to the appended drawings.

BRIEF DESCRIPTION OF THE DRAWINGS

FIG. 1 is an illustration of amino acid sequences (SEQ ID NO:1) corresponding to the base sequences as shown in FIG. 2.

FIG. 2 is an illustration of a deoxyribonucleotide sequence (SEQ ID NO:2) of βIR of a human origin as obtained in Example 3.

FIG. 3 is an illustration of an amino acid sequence (SEQ. ID NO:3) corresponding to the deoxyribonucleotide as shown in FIG. 4.

FIG. 4 is an illustration of a deoxyribonucleotide sequence (SEQ ID NO:4) of mβIR of a mouse origin.

FIG. 6 is an illustration of sequences of PCR primers used in amplifying subregions of the βIR gene of a human origin as described in Example 3, with all the primers, sequences being shown in the direction from 5' to 3' end.

FIG. 8 is an illustration of inhibition of βIR channel activity by a sulfonylurea drug (Glibenclamide) in Example 4.

EXAMPLE 1 cDNA of βIR-1 of a human origin and gene cloning:

In view of the well known fact that the gene encoding the inward rectifier potassium channel has its intron deleted, screening was performed of 7×105 plaque of a λFIXII human genome library. A full-length rat $uK_{ATP}$-1 cDNA labeled with $^{32}p$ was used as a probe under standard hybridization conditions.

The transfer membrane was treated through washing with 2xssc/0.1% SDS at 42° C. for 30 min.

Using a $^{32}$P-labeled human βIR DNA fragment as a probes screening was done on 7×105 plaque of a MIN6 cDNA library of the mouse insulin-secreting cell line under standard hybridization conditions.

The transfer membrane was treated through washing with 0.1×SSC/0.1% SDS at 50° C. for 1 hour.

The two sequences of the DNA chains of human and mouse origins were identified by the dideoxynucleotide chain termination method after subcloning respective DNA fragments with an appropriate length into M13mp18, mp19 and pGEM3Z.

EXAMPLE 2

Figure 5A:
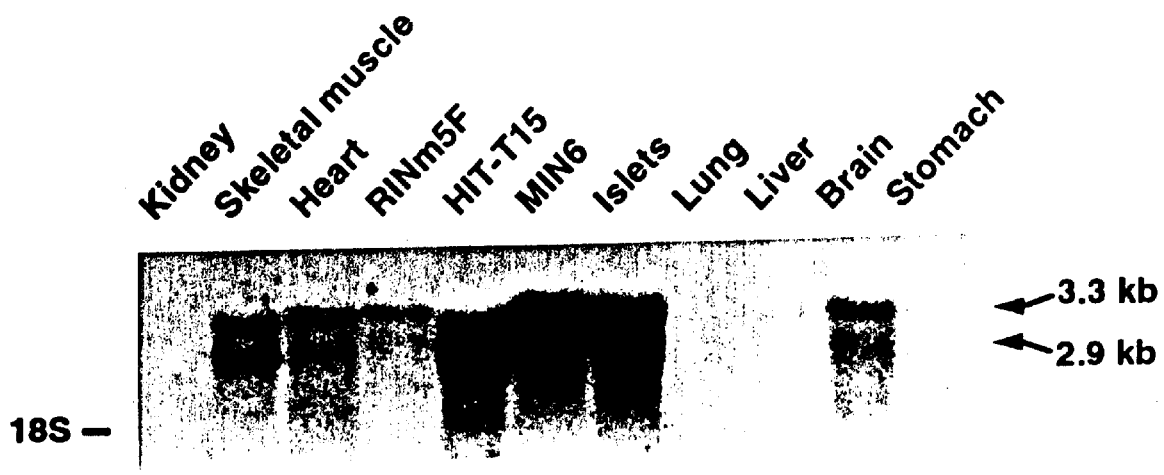
FIG. 5 shows results of RNA blotting analysis of βIR mRNA in various tissues of a rat as described in Example 2.
Figure 5B:
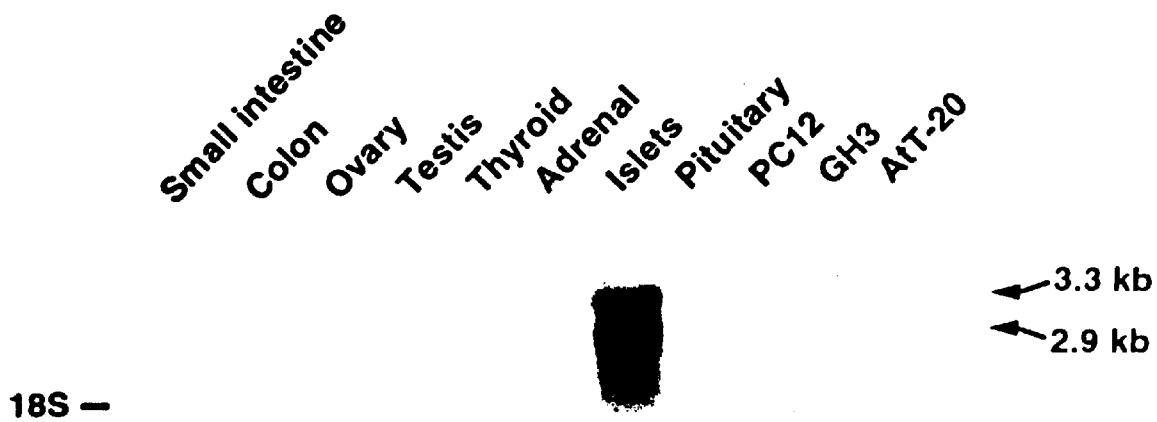
Figure 7A:
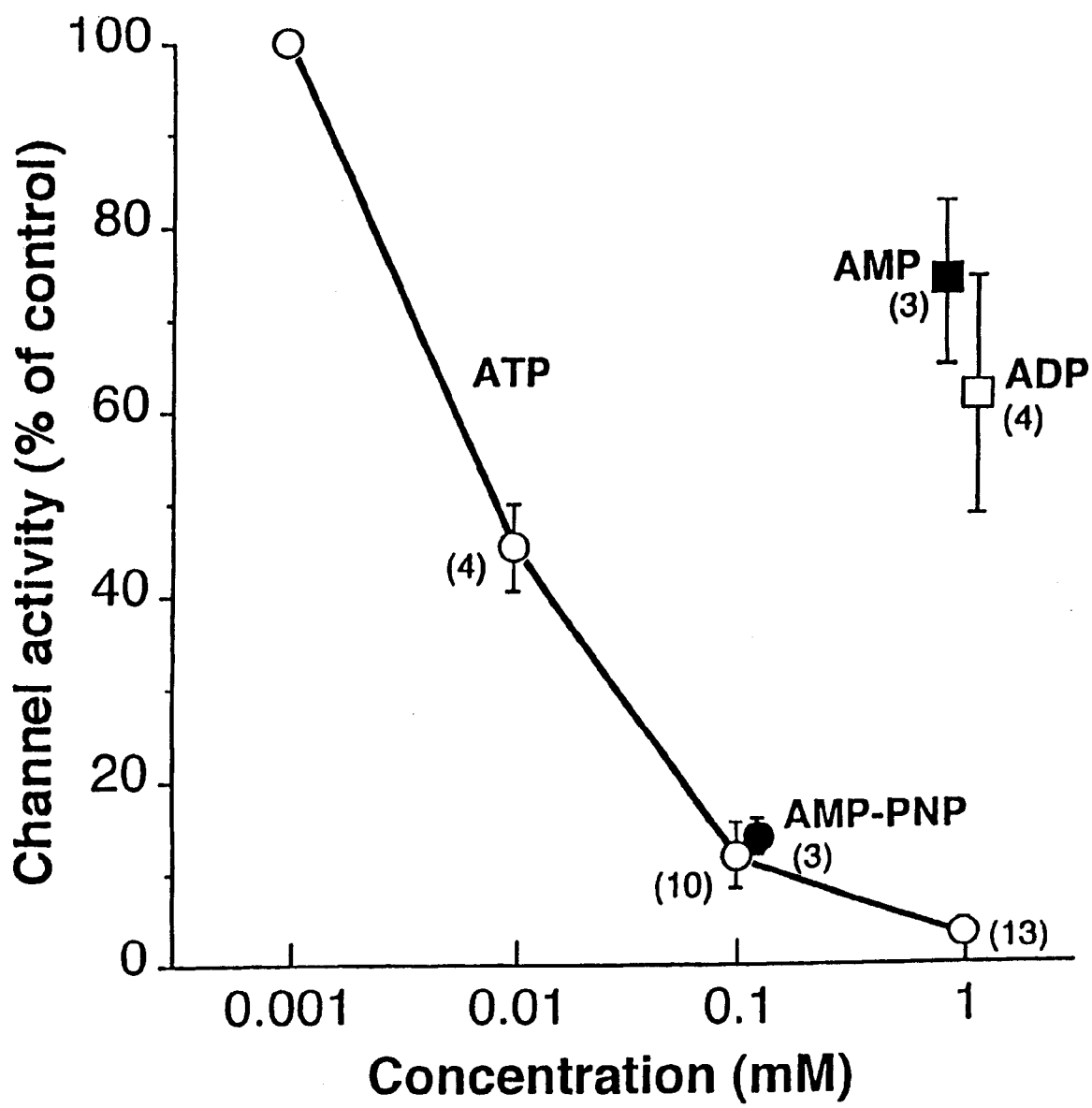
FIG. 7 shows ATP sensitivities of the βIR channel as described in Example 4.
Figure 7B:
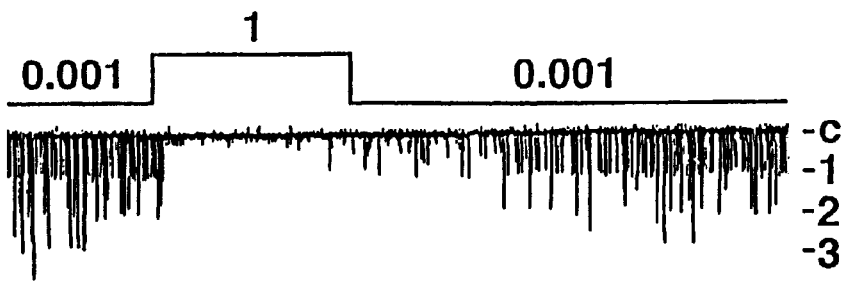
Figure 7C:
Figure 7D:
Figure 7E:
Figure 7F:

RNA blotting analysis:

A 20 μg quantity of RNA extracted from various tissues and cell strains, except for 10 μg each of RNA from the pituitary and thyroid glands, was denatured with formaldehyde, electrophoresed on 1% agarose gel and transferred on a Nylon membrane. Using $^{32}$P-labeled hβIR DNN as a probe, hybridization was conducted.

βIR mRNA was expressed in the pancreatic β-cells and insulin-secreting cell line, namely MIN6 and HITT-15, respectively, at extremely high levels (see FIG. 5).

EXAMPLE 3

PCR-SSCP and DNA sequence:

The genome DNA collected from 20 healthy Japanese subjects was subjected to PCR-SSCP analysis.

Six pairs of Cy5-labeled oligonucleotides were used to enhance the protein coding region of a hβIR-1 gene of human origin (see FIG. 6).

A PCR reaction was carried out in a solution of 10 μl containing 0.1 μg of genome DNA, 10 pmol of sense and anti-sense primers, 10 nmol/l KCl, 20 mmol/l Tris-HCl (pH 8.2), 2.0 mmol/MgCl$_2$, 6 nmol/l (NH$_4$)$_2$SO$_4$, 0.1% Triton X-100, 0.01% bovine serum albumin, 200 μmol of each dNTP and 0.25U of PfuDMA polymerase.

After the first denaturation treatment at 94° C. for 3 min., the specimen was allowed to undergo growth at 40 cycles in the Gene Amp 9600 PCR system, followed by denaturation at 94° C. for 15 sec., annealing at 65° C. or 60° C. for 15 sec. and elongation at 72° C. for 30 sec. The reaction solution containing the specimen was heat-treated at 94° C. for 3 min. and subjected to separation by 5% polyacrylamide gel electrophoresis, followed by DNA sequencing by the automatic sequencer.

EXAMPLE 4

Electro-physiological analysis:

βIR and sulfonylurea receptor were co-expressed in COS-1 cells to conduct electro-physiological analysis, and the potassium channel activity was observed to be suppressed in a ATP-concentration dependent manner (see FIG. 7). Furthermore, the potassium channel activity was found to be inhibited by Glibenclamide, a sulfonylurea drug, as well (see FIG. 8). was observed In order to isolate cDNA encoding $uK_{ATP}$-1 of a human origin, search was effected into a human lung cDNA library using $^{32}$P labeled $ruK_{ATP}$-1 cDNA of a rat origin as a probe. The resultant clone was subjected to sub-cloning into M13mp18, M13mp19 and pGEM3Z, followed by base sequencing by the chain terminator method.

We claim:

1. An isolated deoxyribonucleic acid molecule comprising a base sequence encoding a protein having amino acid SEQ. ID NO:1.

2. The deoxyribonucleic acid molecule of claim 1 having a base sequence represented by SEQ. ID NO:2.

3. The deoxyribonucleic acid molecule of claim 1 wherein the protein exhibits the biological activity of an ATP-sensitive potassium channel protein, said molecule further comprising a base sequence encoding another protein or polypeptide linked to either the 5' end or 3' end of said molecule.

4. The deoxyribonucleic acid molecule of claim 3 having the base sequence represented by SEQ. ID NO:4.

5. An expression plasmid comprising the deoxyribonucleic acid of claim 3 operatively linked to a promoter.

6. An isolated cell transfected with the plasmid of claim 5.

7. An expression plasmid comprising the deoxyribonucleic acid of claim 1 disposed downstream of the promoter of said plasmid.

8. An isolated cell transfected with the plasmid of claim 7.

9. A deoxyribonucleic acid molecule comprising a base sequence encoding the amino acid sequence of SEQ. ID NO:3.

10. An expression plasmid comprising the deoxyribonucleic acid of claim 9 operatively linked to a promoter.

11. An isolated cell transfected with the plasmid of claim 10.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 390 amino acids
      (B) TYPE: amino acid
      (C) STRANDEDNESS: single
      (D) TOPOLOGY: linear (xi) SEQUENCE DESCRIPTION: SEQ ID NO: 1:

```
Met Leu Ser Arg Lys Gly Ile Ile Pro Glu Glu Tyr Val Leu Thr Arg
                  5                  10                  15

Leu Ala Glu Asp Pro Ala Glu Pro Arg Tyr Arg Ala Arg Gln Arg Arg
             20                  25                  30

Ala Arg Phe Val Ser Lys Lys Gly Asn Cys Asn Val Ala His Lys Asn
         35                  40                  45

Ile Arg Glu Gln Gly Arg Phe Leu Gln Asp Val Phe Thr Thr Leu Val
 50                  55                  60

Asp Leu Lys Trp Pro His Thr Leu Leu Ile Phe Thr Met Ser Phe Leu
 65                  70                  75                  80

Cys Ser Trp Leu Leu Phe Ala Met Ala Trp Trp Leu Ile Ala Phe Ala
                 85                  90                  95

His Gly Asp Leu Ala Pro Ser Glu Gly Thr Ala Glu Pro Cys Val Thr
                100                 105                 110

Ser Ile His Ser Phe Ser Ser Ala Phe Leu Phe Ser Ile Glu Val Gln
                115                 120                 125

Val Thr Ile Gly Phe Gly Gly Arg Met Val Thr Glu Glu Cys Pro Leu
130                 135                 140

Ala Ile Leu Ser Leu Ile Val Gln Asn Ile Val Gly Leu Met Ile Asn
145                 150                 155                 160

Ala Ile Met Leu Gly Cys Ile Phe Met Lys Thr Ala Gln Ala His Arg
                165                 170                 175

Arg Ala Glu Thr Leu Ile Phe Ser Lys His Ala Val Ile Ala Leu Arg
                180                 185                 190

His Gly Arg Leu Cys Phe Met Leu Arg Val Gly Asp Leu Arg Lys Ser
                195                 200                 205

Met Ile Ile Ser Ala Thr Ile His Met Gln Val Val Arg Lys Thr Thr
210                 215                 220

Ser Pro Glu Gly Glu Val Val Pro Leu His Gln Val Asp Ile Pro Met
225                 230                 235                 240

Glu Asn Gly Val Gly Gly Asn Ser Ile Phe Leu Val Ala Pro Leu Ile
                245                 250                 255

Ile Tyr His Val Ile Asp Ala Asn Ser Pro Leu Tyr Asp Leu Ala Pro
                260                 265                 270

Ser Asp Leu His His His Gln Asp Leu Glu Ile Ile Val Ile Leu Glu
                275                 280                 285

Gly Val Val Glu Thr Thr Gly Ile Thr Thr Gln Ala Arg Thr Ser Tyr
                290                 295                 300

Leu Ala Asp Glu Ile Leu Trp Gly Gln Arg Phe Val Pro Ile Val Ala
305                 301                 315                 320

Glu Glu Asp Gly Arg Tyr Ser Val Asp Tyr Ser Lys Phe Gly Asn Thr
                325                 330                 335
```

```
Ile Lys Val Pro Thr Pro Leu Cys Thr Ala Arg Gln Leu Asp Glu Asp
            340                 345                 350

His Ser Leu Leu Glu Ala Leu Thr Leu Ala Ser Ala Arg Gly Pro Leu
            355                 360                 365

Arg Lys Arg Ser Val Pro Met Ala Lys Ala Lys Pro Lys Phe Ser Ile
            370                 375                 380

Ser Pro Asp Ser Leu Ser
385                 390
```

(2) INFORMATION FOR SEQ ID NO: 2:

(i) SEQUENCE CHARACTERISTICS:
        (A) LENGTH: 1173 base pairs
        (B) TYPE: nucleic acid
        (C) STRANDEDNESS: single
        (D) TOPOLOGY: linear (xi) SEQUENCE DESCRIPTION: SEQ ID NO: 2:

```
ATGCTGTCCC GCAAGGGCAT CATCCCCGAG GAATACGTGC TGACACGCCT GGCAGAGGAC      60
CCTGCCGAGC CAGGTACCG TGCCCGCCAG CGGAGGGCCC GCTTTGTGTC CAAGAAAGGC      120
AACTGCAACG TGGCCCACAA GAACATCCGG GAGCAGGGCC GCTTCCTGCA GGACGTGTTC      180
ACCACGCTGG TGGACCTCAA GTGGCCACAC ACATTGCTCA TCTTCACCAT GTCCTTCCTG      240
TGCAGCTGGC TGCTCTTCGC CATGGCCTGG TGGCTCATCG CCTTCGCCCA CGGTGACCTG      300
GCCCCCAGCG AGGGCACTGC TGAGCCCTGT GTCACCAGCA TCCACTCCTT CTCGTCTGCC      360
TTCCTTTTCT CCATTGAGGT CCAAGTGACT ATTGGCTTTG GGGGCGCAT GGTGACTGAG       420
GAGTGCCCAC TGGCCATCCT GAGCCTCATC GTGCAGAACA TCGTGGGGCT CATGATCAAC      480
GCCATCATGC TTGGCTGCAT CTTCATGAAG ACTGCCCAAG CCCACCGCAG GGCTGAGACC      540
CTCATCTTCA GCAAGCATGC GGTGATCGCT CTGCGCCACG GCCGCCTCTG CTTCATGCTA      600
CGTGTGGGTG ACCTCCGCAA GAGCATGATC ATCAGCGCCA CCATCCACAT GCAGGTGGTA      660
CGCAAGACCA CCAGCCCCGA GGGCGAGGTG GTGCCCCTCC ACCAGGTGGA CATCCCCATG      720
GAGAACGGCG TGGGTGGCAA CAGCATCTTC CTGGTGGCCC CGCTGATCAT CTACCATGTC      780
ATTGATGCCA ACAGCCCACT CTACGACCTG GCACCCAGCG ACCTGCACCA CCACCAGGAC      840
CTCGAGATCA TCGTCATCCT GGAAGGCGTG GTGGAAACCA CGGGCATCAC CACCCAGGCC      900
CGCACCTCCT ACCTGGCCGA TGAGATCCTG TGGGGCCAGC GCTTTGTGCC CATTGTAGCT      960
GAGGAGGACG GACGTTACTC TGTGGACTAC TCCAAGTTTG GCAACACCAT CAAAGTGCCC     1020
ACACCACTCT GCACGGCCCG CCAGCTTGAT GAGGACCACA GCCTACTGGA AGCTCTGACC     1080
CTCGCCTCAG CCCGCGGGCC CCTGCGCAAG CGCAGCGTGC CCATGGCCAA GGCCAAGCCC     1140
AAGTTCAGCA TCTCTCCAGA TTCCCTGTCC TGA                                 1173
```

(2) INFORMATION FOR SEQ ID NO: 3:

(i) SEQUENCE CHARACTERISTICS:
        (A) LENGTH: 390 amino acids
        (B) TYPE: amino acid
        (C) STRANDEDNESS: single
        (D) TOPOLOGY: linear (xi) SEQUENCE DESCRIPTION: SEQ ID NO: 3:

```
Met Leu Ser Arg Lys Gly Ile Ile Pro Glu Glu Tyr Val Leu Thr Arg
                5                   10                  15

Leu Ala Glu Asp Pro Ala Glu Pro Arg Tyr Arg Thr Arg Glu Arg
            20                  25                  30
```

```
Ala Arg Phe Val Ser Lys Lys Gly Asn Cys Asn Val Ala His Lys Asn
         35                  40                  45

Ile Arg Glu Gln Gly Arg Phe Leu Gln Asp Val Phe Thr Thr Leu Val
 50                  55                  60

Asp Leu Lys Trp Pro His Thr Leu Leu Ile Phe Thr Met Ser Phe Leu
65                   70                  75                  80

Cys Ser Trp Leu Leu Phe Ala Met Val Trp Trp Leu Ile Ala Phe Ala
                 85                  90                  95

His Gly Asp Leu Ala Pro Gly Glu Gly Thr Asn Val Pro Cys Val Thr
                100                 105                 110

Ser Ile His Ser Phe Ser Ser Ala Phe Leu Phe Ser Ile Glu Val Gln
             115                 120                 125

Val Thr Ile Gly Phe Gly Gly Arg Met Val Thr Glu Glu Cys Pro Leu
         130                 135                 140

Ala Ile Leu Ile Leu Ile Val Gln Asn Ile Val Gly Leu Met Ile Asn
145                 150                 155                 160

Ala Ile Met Leu Gly Cys Ile Phe Met Lys Thr Ala Gln Ala His Arg
                165                 170                 175

Arg Ala Glu Thr Leu Ile Phe Ser Lys His Ala Val Ile Thr Leu Arg
                180                 185                 190

His Gly Arg Leu Cys Phe Met Leu Arg Val Gly Asp Leu Arg Lys Ser
             195                 200                 205

Met Ile Ile Ser Ala Thr Ile His Met Gln Val Val Arg Lys Thr Thr
210                 215                 220

Ser Pro Glu Gly Glu Val Val Pro Leu His Gln Val Asp Ile Pro Met
225                 230                 235                 240

Glu Asn Gly Val Gly Gly Asn Gly Ile Phe Leu Val Ala Pro Leu Ile
                245                 250                 255

Ile Tyr His Val Ile Asp Ser Asn Ser Pro Leu Tyr Asp Leu Ala Pro
             260                 265                 270

Ser Asp Leu His His His Gln Asp Leu Glu Ile Ile Val Ile Leu Glu
             275                 280                 285

Gly Val Val Glu Thr Thr Gly Ile Thr Thr Gln Ala Arg Thr Ser Tyr
290                 295                 300

Leu Ala Asp Glu Ile Leu Trp Gly Gln Arg Phe Val Pro Ile Val Ala
305                 301                 315                 320

Glu Glu Asp Gly Arg Tyr Ser Val Asp Tyr Ser Lys Phe Gly Asn Thr
                325                 330                 335

Ile Lys Val Pro Thr Pro Leu Cys Thr Ala Arg Gln Leu Asp Glu Asp
                340                 345                 350

Arg Ser Leu Leu Asp Ala Leu Thr Leu Ala Ser Ser Arg Gly Pro Leu
             355                 360                 365

Arg Lys Arg Ser Val Ala Val Ala Lys Ala Lys Pro Lys Phe Ser Ile
             370                 375                 380

Ser Pro Asp Ser Leu Ser
385                 390

(2) INFORMATION FOR SEQ ID NO: 4:

(i) SEQUENCE CHARACTERISTICS:
        (A) LENGTH:   1173 base pairs
        (B) TYPE:  nucleic acid
        (C) STRANDEDNESS: single
        (D) TOPOLOGY:      linear (xi) SEQUENCE DESCRIPTION: SEQ ID NO: 4:
```

-continued

```
ATGCTGTCCC GAAAGGGCAT TATCCCTGAG GAATATGTGC TGACCCGGCT GGCAGAGGAC          60
CCTGCAGAGC CCAGGTACCG TACTCGAGAG AGGAGGGCCC GCTTCGTGTC CAAGAAAGGC         120
AACTGCAACG TCGCCCACAA GAACATTCGA GAGCAGGGCC GCTTCCTGCA GGATGTGTTC         180
ACCACGCTGG TGGACCTCAA ATGGCCACAC ACTCTGCTCA TTTTCACCAT GTCCTTCCTG         240
TGCAGCTGGC TGCTCTTTGC CATGGTCTGG TGGCTCATCG CCTTCGCCCA CGGTGACCTG         300
GCCCCCGGAG AGGGCACCAA TGTGCCCTGC GTCACAAGCA TCCACTCCTT TTCATCTGCC         360
TTCCTTTTCT CCATCGAGGT CCAGGTGACC ATTGGTTTCG GCGGGCGCAT GGTGACAGAG         420
GAATGTCCCC TGGCCATCCT CATTCTCATT GTGCAGAATA TCGTCGGGCT GATGATCAAC         480
GCCATCATGC TGGGCTGCAT CTTCATGAAA ACGGCCCAGG CCCATCGGCG GGCAGAAACC         540
CTCATCTTCA GCAAGCATGC TGTGATCACC CTGCGCCATG GCCGCCTGTG CTTCATGCTG         600
CGCGTAGGGG ACCTCCGAAA GAGCATGATC ATTAGCGCCA CCATCCACAT GCAGGTGGTG         660
CGCAAGACCA CCAGCCCCGA GGGCGAAGTT GTGCCTCTCC ACCAGGTAGA CATCCCCATG         720
GAGAATGGCG TGGGTGGTAA CGGCATCTTC CTGGTGGCCC CACTCATCAT CTACCACGTC         780
ATCGACTCCA ACAGCCCGCT CTACGACCTG GCTCCTAGTG ACCTGCACCA CCACCAGGAC         840
CTGGAGATCA TTGTCATCTT GGAAGGCGTG GTAGAAACCA CGGGCATCAC CACCCAGGCC         900
CGCACCTCCT ACCTAGCTGA CGAGATTCTA TGGGGGCAGC GCTTTGTCCC CATTGTGGCC         960
GAGGAGGACG GCCGCTATTC TGTGGACTAC TCCAAATTTG GTAACACCAT TAAAGTGCCC        1020
ACACCACTCT GCACAGCCCG CCAGCTTGAT GAGGACCGCA GTCTGCTGGA TGCCCTGACC        1080
CTCGCCTCGT CGCGGGGCC CCTGCGCAAG CGCAGTGTGG CTGTGGCGAA GGCCAAGCCC        1140
AAGTTTAGCA TCTCTCCAGA TTCCTTGTCC TGA                                    1173
```